United States Patent
Huchede et al.

(10) Patent No.: US 12,415,775 B2
(45) Date of Patent: Sep. 16, 2025

(54) PROCESS FOR THE PREPARATION OF HEXAMETHYLENEDIAMINE BY HYDROGENATION OF ADIPONITRILE WITH REDUCED FORMATION OF DIAMINOCYCLOHEXANE

(71) Applicant: BASF SE, Ludwigshafen am Rhein (DE)

(72) Inventors: Maxime Huchede, Lyons (FR); Sandra Chouzier, Deaux (FR)

(73) Assignee: BASF SE, Ludwigshafen Am Rhein (DE)

(*) Notice: Subject to any disclaimer, the term of this patent is extended or adjusted under 35 U.S.C. 154(b) by 506 days.

(21) Appl. No.: 17/913,175

(22) PCT Filed: Mar. 24, 2021

(86) PCT No.: PCT/EP2021/057587
§ 371 (c)(1),
(2) Date: Sep. 21, 2022

(87) PCT Pub. No.: WO2021/191288
PCT Pub. Date: Sep. 30, 2021

(65) Prior Publication Data
US 2023/0150918 A1    May 18, 2023

(30) Foreign Application Priority Data
Mar. 25, 2020 (EP) .................... 20165605

(51) Int. Cl.
C07C 209/26 (2006.01)
C07C 209/28 (2006.01)
C07C 211/12 (2006.01)

(52) U.S. Cl.
CPC .......... *C07C 209/26* (2013.01); *C07C 209/28* (2013.01); *C07C 211/12* (2013.01)

(58) Field of Classification Search
None
See application file for complete search history.

(56) References Cited

U.S. PATENT DOCUMENTS

| | | |
|---|---|---|
| 3,235,600 A | 2/1966 | Evans |
| 3,821,305 A | 6/1974 | Bartalini et al. |
| 3,917,707 A | 11/1975 | Williams et al. |
| 4,429,159 A | 1/1984 | Cutchens et al. |
| 2001/0004672 A1 | 6/2001 | Degischer et al. |
| 2005/0101797 A1 | 5/2005 | Allgeier |
| 2008/0039658 A1 | 2/2008 | Amakawa et al. |
| 2008/0214387 A1 | 9/2008 | Ostgard et al. |
| 2009/0069603 A1 | 3/2009 | Hahn et al. |
| 2009/0264679 A1 | 10/2009 | Ostgard et al. |

FOREIGN PATENT DOCUMENTS

| | | |
|---|---|---|
| JP | 51-041307 A | 4/1976 |
| JP | 59-181242 A | 10/1984 |
| JP | 2001-212461 A | 8/2001 |
| JP | 2008-063326 A | 3/2008 |
| JP | 2008-519677 A | 6/2008 |
| JP | 2008-522818 A | 7/2008 |
| WO | 2006/050749 A1 | 5/2006 |
| WO | 2014/099610 A1 | 6/2014 |

OTHER PUBLICATIONS

International Search Report and Written Opinion received for PCT Patent Application No. PCT/EP2021/057587, mailed on Jun. 15, 2021, 9 pages.

*Primary Examiner* — Renee Claytor
*Assistant Examiner* — Jennifer C Sawyer
(74) *Attorney, Agent, or Firm* — Faegre Drinker Biddle & Reath LLP

(57) ABSTRACT

The present invention relates to a process for the preparation of hexamethylenediamine by hydrogenation of adiponitrile in the presence of a Raney nickel catalyst, wherein a Raney nickel catalyst modified by treatment with carbon monoxide or carbon dioxide in a liquid medium is used.

12 Claims, No Drawings

PROCESS FOR THE PREPARATION OF HEXAMETHYLENEDIAMINE BY HYDROGENATION OF ADIPONITRILE WITH REDUCED FORMATION OF DIAMINOCYCLOHEXANE

CROSS-REFERENCE TO RELATED APPLICATIONS

This application is a national stage application (under 35 U.S.C. § 371) of PCT/EP2021/057587, filed Mar. 24, 2021, which claims benefit of European Application No. 20165605.5, filed Mar. 25, 2020, both of which are incorporated herein by reference in their entirety.

TECHNICAL FIELD

The present invention relates to a process for the preparation of hexamethylenediamine by hydrogenation of adiponitrile in the presence of a Raney nickel catalyst.

BACKGROUND ART

Hexamethylenediamine is a compound used in numerous applications, the main ones of which are the manufacture of polyamides such as poly(hexamethylene adipamide), more commonly known as PA 6,6, and the manufacture of hexamethylene diisocyanate.

Several processes for manufacturing hexamethylenediamine have been proposed, which generally consist of a hydrogenation of adiponitrile (tetramethylene dicyanide) in the presence of a hydrogenation catalyst. Two types of process are utilized industrially that use different catalysts and different temperature and pressure conditions.

Thus, a first type of hydrogenation process that is utilized and described in the literature consists in hydrogenating nitrile compounds in the presence of ammonia and under high pressure, with a ruthenium-based catalyst for example. Iron based catalysts under high pressure and temperature are also used.

A second type of process consists in carrying out the hydrogenation of nitrile compounds under pressure and at a not very high temperature, for example at 25 bar and 80° C., in the presence of a basic compound and a catalyst based on Raney nickel.

In the latter type of process, the hydrogenation of nitrile compounds to amines takes place in the presence of a catalyst based on optionally doped Raney nickel. These catalysts are prepared by the leaching of aluminium, from Ni—Al alloys, in a strongly alkaline medium. The catalysts obtained are composed of agglomerates of nickel crystallites, having a high specific surface area and a variable residual aluminium content.

It is known that adiponitrile can react by hydrogenation to give a cyclic diamine, diaminocyclohexane (DCH). However, DCH is particularly troublesome since it has a boiling point close to the boiling point of the targeted amine and is therefore very difficult to separate.

There is an industrial need for optimization of the hydrogenation of adiponitrile to hexamethylenediamine, by means of Raney nickel catalysts, especially with respect to the activity, the selectivity and the deactivation behaviour of the final catalyst. In particular, it is important to limit the formation of diaminocyclohexane in order to obtain a hexamethylenediamine which can be purified with a minimum capital cost and a minimum energy consumption.

U.S. Pat. No. 3,235,600 concerns a process for the catalytic hydrogenation of adiponitrile to hexamethylenediamine, wherein the production of the by-product 1,2-diaminocyclohexane (DCH) is suppressed. The document generally describes a process wherein a mixture of adiponitrile, ammonia, hydrogen, and a DCH suppressing compound selected from organic and inorganic carbonates, organic and inorganic carbamates and carbon dioxide is passed over or through a hydrogenation catalyst under conditions of elevated temperature and pressure. As hydrogenation catalysts, nickel, cobalt, copper, zinc, platinum, palladium, rubidium, and ruthenium, either in the form of free metals or in the form of compounds such as the oxides or salts, are mentioned. For the hydrogenation of adiponitrile to hexamethylenediamine, cobalt catalysts and in particular catalysts comprising cobalt oxide are preferred. In the examples, hexamethylenediamine carbonate and aminocapronitrile carbamate are used as DCH suppressants with a sintered pelleted cobalt catalyst. A pre-treatment of the catalyst prior to hydrogenation is not disclosed.

It is an object of the present invention to provide a process for the preparation of hexamethylenediamine by hydrogenation of adiponitrile in the presence of a Raney nickel catalyst which is characterized in a low formation of diaminocyclohexane (DCH) as side product.

SUMMARY OF THE INVENTION

The object is achieved by a process for the preparation of hexamethylenediamine by hydrogenation of adiponitrile in the presence of a Raney nickel catalyst, wherein a Raney nickel catalyst modified by treatment with carbon monoxide or carbon dioxide in a liquid medium is used.

DETAILED DESCRIPTION

In one embodiment of the invention, the Raney nickel catalyst has been modified by pre-treatment with carbon monoxide in pure form, in an inert gas or in hydrogen, preferably in hydrogen, prior to hydrogenation.

In general, carbon monoxide is applied in a concentration of from 50 to 1000 ppm, preferably from 100 to 500 ppm, in particular from 150 to 350 ppm in hydrogen.

In a further embodiment, the Raney nickel catalyst has been modified by pre-treatment with carbon dioxide in an inert gas prior to hydrogenation.

In general, in carbon dioxide is applied in a concentration of from 1 to 100 vol.-%, preferably from 1 to 25 vol.-% in an inert gas. Pure carbon dioxide can be also used.

Suitable inert gases are for example nitrogen and argon. In one particular embodiment, argon is used as inert gas.

In the pre-treatment step, the liquid medium is preferably water.

In the pre-treatment step, the pulverulent Raney nickel catalyst is contacted in a liquid medium with the pretreatment gas containing carbon monoxide in hydrogen or carbon dioxide in an inert gas. The contacting can be carried out by stirring the pulverulent Raney nickel catalyst in an autoclave.

In general, the pre-treatment is carried out at a total pressure of from 1 to 50 bar, preferably from 2 to 50 bar, more preferably from 5 to 30 bar, and in general at a temperature of from 0 to 40° C., preferably from 10 to 30° C. For example, the pretreatment can be carried out during a time of from 5 to 120 min, preferably from 15 to 60 min.

In a further embodiment, the Raney catalyst is modified during hydrogenation by adding carbon monoxide or carbon dioxide to the hydrogenation gas. In this embodiment, no separate pretreatment step is necessary. In certain embodiments, carbon monoxide is added in general in a concentration of from 50 to 1000 ppm, preferably from 100 ppm to 500 ppm, in particular 150 to 350 ppm to the hydrogenation gas.

The hydrogenation reaction is in general carried out in the presence of a solvent advantageously composed of the amine obtained by the hydrogenation. Thus, in the case of the hydrogenation of adiponitrile, hexamethylenediamine is advantageously used as main component of the reaction medium. The concentration of amine in the reaction medium is advantageously between 50% and 99% by weight, preferably between 60 and 99% by weight, of the liquid phase of the hydrogenation reaction medium.

The hydrogenation reaction is preferably carried out in the presence of water as other component of the reaction medium. This water is generally present in an amount of less than or equal to 50% by weight, advantageously of less than or equal to 20% by weight, in the liquid phase of the total reaction medium and more preferably still between 0.1% and 15% by weight. Organic solvents can also be used as other component of the reaction medium.

The hydrogenation reaction is carried out in the presence of a basic compound, preferably an inorganic base, such as LiOH, NaOH, KOH, RbOH, CsOH and their mixtures. NaOH and KOH are preferably used.

The amount of base added is determined in order to have at least 0.1 mol of base per kilogram of catalyst, preferably between 0.1 and 2 mol of base per kg of catalyst and more advantageously still between 0.3 and 1.5 mol of base per kg of catalyst.

The hydrogenation reaction is in general carried out at a temperature of less than or equal to 150° C., e.g. from 50 to 150° C., preferably of less than or equal to 120° C. and more preferably of less than or equal to 100° C. The reaction temperature is most preferably from 50° C. to 100° C.

The hydrogen pressure in the reactor is in general from 1 to 100 bar (0.10 and 10 MPa), preferably from 10 to 50 bar (1 to 5 MPa).

The Raney nickel catalyst used according to the invention can advantageously comprise one or more other elements, often referred to as dopants, such as, for example, chromium, titanium, molybdenum, tungsten, manganese, vanadium, zirconium, iron, zinc and more generally the elements from groups IIB, IVB, IIIB, VB, VIB, VIIB and VIII of the Periodic Table of the Elements. Among these dopant elements, chromium, iron and/or zinc or a mixture of these elements are considered as being the most advantageous and are usually present at a concentration by weight (expressed relative to the Raney nickel metal) of less than 10%, preferably less than 5%. For example, the concentration of iron may be from 1 to 2% by weight, the concentration of chromium may be from 0.5 to 5% by weight and the concentration of zinc may be from 0.5 to 5% by weight.

Raney catalysts often comprise traces of metals present in the alloy used to prepare the said catalysts. Thus, aluminium is especially present in these catalysts. The concentration of aluminium may be from 2 to 10% by weight.

The optionally doped Raney Ni catalyst generally originates from a molten Ni—Al precursor alloy (Ni content for example from 28 to 59% by weight), to which metallic dopant elements, preferably iron, chromium and zinc, are added according to a doping procedure known as a "metallurgical" doping procedure. After cooling and grinding, the doped precursor alloy is subjected, in a conventional manner, to an alkaline attack that gives rise to a greater or lesser removal of aluminium and, optionally, of a fraction of the dopant element. The starting alloys used are, advantageously, chosen from the following forms of binary nickel/aluminium combinations: $NiAl_3$, $Ni_2Al_3$ and proeutectic $Al/NiAl_3$.

It is also possible to introduce dopants via "chemical" doping by impregnating the Raney Ni catalyst with a solution containing a precursor of the dopant element, by precipitating the dopant element on the Raney Ni catalyst, or by introducing the precursor compound of the dopant during the alkaline attack of the Raney alloy.

The present invention is further illustrated by the following examples. It should be understood that the following examples are for illustration purposes only, and are not used to limit the present invention thereto.

EXAMPLES

Impurities amount was determined by gas chromatography using an internal standard.

Two general procedures were used to respectively measure catalytic activity and selectivity with a modified and unmodified catalyst. The catalytic activity was determined in a batch reactor whereas selectivity was measured in a semi-continuous reactor.

Two modification agents were used: carbon monoxide (CO) and carbon dioxide ($CO_2$). For both, a general procedure was used to pretreat the nickel Raney catalyst in a liquid medium consisting of water or other organic solvent. And hydrogenation was then conducted with pure hydrogen.

For CO, ADN hydrogenation was also conducted in 250 ppm of CO in $H_2$ overall pressure, with an unmodified catalyst.

Example 1: General Procedure for Catalytic Activity Measurement

In a dry atmosphere of $N_2$, 0.19 g of nickel Raney catalyst were stirred with 2.8 g of water and 24.6 g of pure hexamethylenediamine and 20 μL of an aqueous solution of potassium hydroxide at 7 mol/L, corresponding to 0.8 mol of OH—/kg of Ni. The temperature was raised at 80° C. and 25 bar of hydrogen overall pressure. 2.5 g of adiponitrile were added in one time in the autoclave and were hydrogenated. In those operating conditions, the catalytic activity is $90 \times 10^{-5}$ mol $H_2/g_{catalyst}$/s.

Example 2: General Procedure for Selectivity Measurement

In a dry atmosphere of $N_2$, 1.1 g of unmodified nickel Raney catalyst were stirred with 1.7 g of water and 15.2 g of pure hexamethylenediamine and 129 μL of an aqueous solution of potassium hydroxide at 7 mol/L, corresponding to 0.8 mol of OH—/kg of Ni. The temperature was raised at 80° C. and 25 bar of hydrogen overall pressure. 10 g of adiponitrile (ADN) were added dropwise in the autoclave and were hydrogenated. After 3 hours, the crude hexamethylenediamine produced was analyzed by gas chromatography. 0.1939% of 1,2-diaminocyclohexane (DCH) were produced in those operating conditions.

Example 3: General Procedure for Catalyst Deactivation Measurement

At the end of ADN addition in the previous example, 2.5 g of ADN were added in one time in the autoclave containing the used catalyst and the crude HMD produced in example 2 (no emptying of the reaction mixture) and were hydrogenated (25 bar, 80° C.). In those operating conditions, the catalytic activity is $37.4 \times 10^{-5}$ mol $H_2/g_{catalyst}/s$ which represents 58% of activity loss (compared to reference $90 \times 10^{-5}$ mol $H_2/g_{catalyst}/s$)

Example 4: General Procedure for Catalyst Modification Pretreatment

The procedure of example 1 and 2 were followed except that prior to hydrogenation, 2 g of nickel Raney catalyst were stirred with 80 g of water at room temperature with 20 bar of 250 ppm of CO in $H_2$ or 10 vol.-% $CO_2$ in argon for 30 min. The modified catalyst was then decanted off and used for adiponitrile hydrogenation with pure hydrogen.

The catalytic activity and the weight percent of 1,2-diaminocyclohexane (DCH) in the crude hexamethylenediamine are reported in Table 1 below.

TABLE 1

| Catalyst | Activity ($10^{-5}$ mol $H_2$/g/s) | % of [DCH] | % of decrease |
|---|---|---|---|
| Unmodified (reference) | 90 | 0.1939 | x |
| Modified with CO/$H_2$ | 77 | 0.1922 | −2.6% |
| Modified with $CO_2$/Ar | 61 | 0.1208 | −38% |

Catalyst modification with $CO_2$ allows to reduce DCH and also all impurities from HMD process. Indeed, the total amount of impurities decreases from 0.2540% (reference experiment) to 0.1710%.

Example 5: Hydrogenation of Adiponitrile with 250 ppm of CO in $H_2$

The procedure of example 1 and 2 were followed except that the pure hydrogen used for adiponitrile hydrogenation was substituted with 250 ppm of CO in $H_2$.

Procedure for Catalytic Activity Measurement Under 250 ppm CO in $H_2$

In a dry atmosphere of $N_2$, 0.48 g of nickel Raney catalyst were stirred with 7.3 g of water and 65.6 g of pure hexamethylenediamine and 55 µL of an aqueous solution of potassium hydroxide at 7 mol/L, corresponding to 0.8 mol of OH—/kg of Ni. The temperature was raised at 80° C. and 25 bar of 250 ppm CO in hydrogen overall pressure. 7.2 g of adiponitrile (ADN) were added in one time in the autoclave and were hydrogenated. In those operating conditions, the catalytic activity is $96 \times 10^{-5}$ mol $H_2/g_{catalyst}/s$.

Procedure for Selectivity Measurement Under 250 ppm CO in $H_2$

In a dry atmosphere of $N_2$, 3 g of nickel Raney catalyst were stirred with 4.5 g of water and 40.5 g of pure hexamethylenediamine and 345 µL of an aqueous solution of potassium hydroxide at 7 mol/L, corresponding to 0.8 mol of OH—/kg of Ni. The temperature was raised at 80° C. and 25 bar of 250 ppm CO in hydrogen overall pressure. 30 g of adiponitrile (ADN) were added dropwise at a mass flow of 10 g/h in the autoclave and were hydrogenated. After 3 hours, the crude hexamethylenediamine produced was analyzed by gas chromatography. 0.1633% of 1,2-diaminocyclohexane (DCH) were produced in those operating conditions.

The catalytic activity and the weight percents of 1,2-diaminocyclohexane in the crude hexamethylenediamine are reported in Table 2 below.

TABLE 2

| Catalyst | Activity ($10^{-5}$ mol $H_2$/g/s) | % of [DCH] | % of decrease |
|---|---|---|---|
| Pure $H_2$ (reference) | 111 | 0.1939 | x |
| 250 ppm of CO in $H_2$ | 96 | 0.1633 | −10% |

Example 6: Deactivation of the Catalyst

The procedure of example 3 was followed for each experiments. The catalytic activities of the used nickel Raney catalysts are reported in Table 3 below.

TABLE 3

| Co-catalyst | Activity ($10^{-5}$ mol $H_2$/g/s) | Activity loss (%) |
|---|---|---|
| Unmodified (reference) | 37.4 | −58% |
| Modified with $CO_2$/Ar | 27.9 | −54% |

No pronounced effect on catalyst deactivation was observed.

The invention claimed is:

1. A process for the preparation of hexamethylenediamine by hydrogenation of adiponitrile in the presence of a Raney nickel catalyst, wherein the Raney nickel catalyst is modified by treatment with carbon monoxide or carbon dioxide in a liquid medium.

2. The process according to claim 1, wherein the Raney nickel catalyst has been modified by pre-treatment with carbon monoxide in hydrogen prior to the hydrogenation.

3. The process according to claim 2, wherein carbon monoxide is applied in a concentration of from 50 to 1000 ppm in hydrogen.

4. The process according to claim 1, wherein the Raney nickel catalyst has been modified by pre-treatment with carbon dioxide in an inert gas prior to the hydrogenation.

5. The process according to claim 4, wherein carbon dioxide is applied in a concentration of from 1 to 25 vol.-% in an inert gas.

6. The process according to claim 5, wherein the inert gas is argon.

7. The process according to claim 2, wherein the pre-treatment is carried out in water.

8. The process according to claim 2, wherein the pre-treatment is carried out at a total pressure of from 2 to 50 bar at a temperature of from 0 to 40° C.

9. The process according to claim 1 wherein the Raney nickel catalyst is modified during hydrogenation by adding carbon monoxide to the hydrogenation gas.

10. The process according to claim 9, wherein carbon monoxide is added in a concentration of from 50 to 1000 ppm to the hydrogenation gas.

11. The process according to claim 1, wherein the hydrogenation is carried out at a temperature of from 50 to 150° C. at a hydrogen pressure of from 1 to 100 bar.

12. The process according to claim 4, wherein the pre-treatment is carried out in water.

* * * * *